United States Patent [19]

Strasser et al.

[11] Patent Number: 5,099,085
[45] Date of Patent: Mar. 24, 1992

[54] CHLORINATION REACTIONS AND OXYCHLORINATION REACTIONS IN THE PRESENCE OF HONEYCOMB MONOLITHIC CATALYST SUPPORTS

[75] Inventors: Rudolf Strasser, Burghausen; Ludwig Schmidhammer, Haiming; Klaus Deller, Hainburg; Helmfried Krause, Rodenbach, all of Fed. Rep. of Germany

[73] Assignees: Wacker Chemie GmbH, Munich; Degussa Ag, Frankfurt, both of Fed. Rep. of Germany

[21] Appl. No.: 664,468

[22] Filed: Mar. 1, 1991

Related U.S. Application Data

[63] Continuation of Ser. No. 433,521, Nov. 8, 1989, abandoned.

[30] Foreign Application Priority Data

Nov. 17, 1988 [DE] Fed. Rep. of Germany ....... 3838811

[51] Int. Cl.⁵ .......................................... C07C 17/156
[52] U.S. Cl. .................................. 570/245; 570/243; 570/253; 570/254; 570/224; 570/227; 570/228; 570/234
[58] Field of Search ............... 570/243, 245, 254, 253, 570/224, 227, 228, 234

[56] References Cited

U.S. PATENT DOCUMENTS

| | | | |
|---|---|---|---|
| 3,948,810 | 4/1975 | Hervert | 502/527 |
| 4,280,926 | 7/1981 | Kazunobu et al. | 502/527 |
| 4,460,699 | 7/1984 | Convers et al. | 570/243 |

*Primary Examiner*—Howard T. Mars
*Attorney, Agent, or Firm*—Burgess, Ryan & Wayne

[57] ABSTRACT

The use of hitherto known supported catalysts in chlorination processes and oxychlorination processes leads to high pressure drops and to the formation of hot spot temperatures in the reactor. When honeycomb monolithic catalyst supports provided with a multiplicity of channels open at both ends and parallel to the longitudinal axis are used, both the heat dissipation is improved and the pressure drops across the reactor are lowered drastically. This leads ultimately to an increase in the selectivity of the reaction and to a minimization of the combustion rate.

12 Claims, 2 Drawing Sheets ns 5,099,085

CHLORINATION REACTIONS AND OXYCHLORINATION REACTIONS IN THE PRESENCE OF HONEYCOMB MONOLITHIC CATALYST SUPPORTS

This application is a continuation, of application Ser. No. 433,521, filed Nov. 8, 1989 now abandoned.

FIELD OF THE INVENTION

The invention is the use of honeycomb monolithic catalyst supports, preferably for selective chlorination reactions and/or oxychlorination reactions in tube-bundle reactors with a fixed-bed arrangement of the catalyst.

The chlorination and oxychlorination reactions can be used for the production of saturated or unsaturated monochlorinated or polychlorinated hydrocarbons from saturated and unsaturated hydrocarbons or partially chlorinated hydrocarbons.

Selective chlorination reactions and/or oxychlorination reactions, for example the conversion of ethylene-containing waste gases with chlorine to 1,2-dichloroethane, or the conversion of ethylene with hydrogen chloride and air and/or oxygen to 1,2-dichloroethane and water or the conversion of methane with chlorine and/or hydrogen chloride and air and/or oxygen to chlorinated methanes, or the reaction of ethane with chlorine to vinyl chloride and chlorinated ethanes, are frequently carried out in reactors over fixed-bed catalysts, with the reactants in the gaseous form. The actual reaction takes place in the gas/solid transition region. The gaseous reactants pass over the solid catalyst, at elevated temperatures and pressures, and react with one another at the gas/solid phase boundary. The products thus formed, together with the unconverted part of the gas stream, leave the reactor and are then separated by suitable process engineering measures from the unconverted part.

Most of the reactions just mentioned are highly exothermic. For better thermal control, the reaction is frequently pulled apart, in a manner of speaking, by connecting several reactors in series. Cooling of the reactors is generally effected by vaporizing hot water under pressure or by means of a heat transfer medium which, depending on the required temperature level, can be, for example, a hydrocarbon fraction, a heat transfer oil or a salt melt. Conventionally, reactors of this type, for exothermic reactions consist of many tubes, in which the catalyst is located and which are surrounded by a cooling jacket through which the above-mentioned cooling media are passed.

RELATED ART

The catalysts comprise a support material and an active catalytic component. Usually, the support material is activated alumina, aluminum silicate, silica gel or a similar surface-active material. With respect to the form and shape of the catalyst support, for example, moldings of spherical shape are used according to German Offenlegungsschrift 2,630,938 (corresponding to U.S. Pat. No. 4,206,180), particles in a cylindrical form (hollow cylinders) are used according to German Offenlegungsschrift 3,113,179 (Corresponding to U.S. Pat. No. 4,366,093) or moldings of columnar geometry are used according to German Offenlegungsschrift 3,607,449 (Corresponding to EP-A 240,714). The active component having a catalytic effect comprises in most cases chlorides and/or an oxides, or oxychlorides of metals, or combinations of these metals with promoters such as alkali metal chlorides, alkaline earth metal chlorides or rare earth metal chlorides. Chlorides, oxides, and oxychlorides of metals such as copper, manganese, iron, cobalt, nickel or platinum generally have catalytic properties effective for these special applications.

In addition, for better control of the heat released by the exothermic reaction, catalysts are frequently used, the active components of which have a concentration profile which rises in a defined manner in the direction of flow, or which have an activity increasing in the direction of flow or which partially contain the active component diluted with an inert material such as, for example, graphite (EP-A 60,317). The different activity levels of such a catalyst are in fact obtained either by changing the concentration of active component and/or by varying the metal salt/promoter molar ratio (cf. German Offenlegungsschrift 2,630,938).

A disadvantage in chlorination processes and oxychlorination processes of the type described above is that the gas (hydrocarbons, chlorine and hydrogen chloride, air and/or oxygen and excess inert gases) passes through the reactors at a high rate, resulting in a relatively large pressure drop across the individual reactors, which makes the use of blowers or compressors necessary in order to drive the gas at the desired rates through the reactors. The expense required for this is considerable.

It is therefore an object to minimize the pressure drop by process engineering measures. A further object is to suppress as far as possible the formation of localized points of overheating, so-called hot spots, in selective chlorination reactions and oxychlorination reactions and thus to increase the yield of the target product.

BRIEF DESCRIPTION OF THE INVENTION

The aforesaid objects are achieved by the use of a monolithic catalyst support having a multiplicity of channels, arranged parallel to the longitudinal axis of the support and open at both ends. The catalyst support has a length corresponding at least to its diameter and preferably to a multiple thereof. The support is provided with the catalyst substance on its surface, which may be coated with a catalysis-promoting material. The novel catalyst is useful in tube-bundle reactors for selective chlorination reactions and/or oxychlorination reactions, in particular for the production of chlorinated hydrocarbons.

DETAILED DESCRIPTION OF THE INVENTION

Honeycomb monolithic catalyst supports have hitherto been used predominantly for the detoxification of automobile exhaust gases (DE-A 1,442,653, DE-A 3,100,930). In these processes, such high reaction temperatures prevail that coking of the catalyst matrix need not be feared, since any coke formed is burned off with oxygen even in statu nascendi. On the other hand, in conventional chlorination catalysts and/or oxychlorination catalysts in the form of a fixed or fluid bed, of particulate material, coke deposits form even in the particle interior. Coke deposits in the particle interior causes the bed material to disintegrate due to bursting and the pressure drop in the catalyst bed can rise drastically. Therefore, it had to be feared that, in the use according to the invention of monolithic catalyst supports for chlorination reactions and/or oxychlorination reactions of this type, the very fine channels are blocked by coke deposition. Surprisingly, however, this is not the case.

Suitability for use in the chlorination or oxychlorination field according to the invention was unexpected from the use, indicated in EP-A 40,660, of honeycomb catalysts for oxidation processes and dehydrogenation processes such as the use for oxidation reactions for the production of ethylene oxide, phthalic acid and maleic acid anhydride (DE-A 3,213,413) or the use generally suggested in DE-A 3,521,767, for exothermic and endothermic chemical reactions having a high heat of reaction with the use of static mixer elements between individual honeycomb elements.

The monolithic catalyst supports have a length from a few centimeters up to about 20 cm and a cross-sectional shape corresponding to the reactor tubes, the internal diameter of the reactor tubes for such highly exothermic reactions being usually 20 to 50 mm.

The cross-sectional shape can be as desired, and preferably the cross-section is circular and the diameter of the support is slightly smaller than the internal diameter of the reaction tubes. Preferably, the diameter/length ratio is about 1:5 to 1:10.

The materials used for preparing such catalyst supports are in principle all those which have hitherto also been used for conventional catalyst moldings; for example, activated alumina, aluminum silicate, silica gel, titanium oxide, silicon carbide or mixtures of these materials, or sintered ceramics of, for example, $\alpha$-Al$_2$O$_3$.

However, mullite or cordierite are preferred. The supports are treated in such a way that, in the final state, they have porous surfaces. This can be effected, for example, by production technology measures or single or repeated coating of a low-porosity or non-porous support with alumina or hydrated SiO$_2$ and subsequent heat treatment of these coatings.

The specific surface area required for the gas/solid state transition in the reaction can be regulated by using materials which are surface-active per se, or by coating with surface-active materials such as, for example, $\gamma$-alumina.

The catalyst supports are provided with channels arranged parallel to the longitudinal axis and open at both ends. The geometry of the cross-section of the channels can be as desired. The diameter and the number of channels, and hence the size of the external surface of the honeycomb catalyst supports, are adapted to the particular reaction. Preferably, the diameter is between 0.1 and 5.0 mm. The preferred range for the number of channels is 10 to 100 per cm$^2$ of cross-sectional area of the support.

The finished moldings are then impregnated, in accordance with the use according to the invention, with the usual active components or mixtures of active component and promoter in the known concentrations. Preferably, the impregnation of the support is carried out by immersion and soaking in the corresponding solutions of the active components.

The reactor tubes are charged in a simple manner by pushing the catalyst supports, provided with active catalyst substance, individually one after the other into the tubes. With a predetermined arrangement of the catalyst supports-and hence also with a predetermined arrangement of the free volume in the reactor tube—the pressure drop across the reactor can be predetermined exactly and minimized by the hole diameter and/or the number of cells per unit area in each individual catalyst module, and also by fitting of spacing of preferably spherical packing between the individual modules. This spacing is adjusted here in such a way that, during charging, catalyst moldings and, for example, glass spheres are introduced alternately into the reaction tube. Preferably, the diameter of the glass spheres is between three and six millimeters.

The preferred embodiment of the invention is therefore based on the use of the catalyst support in a series-connected multiple arrangement of the catalyst within individual tubes of the tubebundle reactor, preferably with the interposition of preferably spherical packing for spacing.

The honeycomb monolithic catalyst support to be used according to the invention has the advantage that its density is very low and hence not much support mass is needed for filling a given reactor volume (Cost reduction). Due to the multiplicity of channels in the longitudinal direction, the external surface area of the catalyst support per unit volume is greatly increased as compared with conventional fixed-bed catalysts, whereby the catalytic activity is enhanced. Moreover, the diffusibility of the gaseous reactants is increased by the porous surface. Since the diffusion of the gaseous reactants is the rate-determining step in such chlorination reactions or oxychlorination reactions, the catalytic activity is enhanced further. The formation of undesired by-products, caused by inadequate diffusion, is reduced. Likewise, the pressure drop across the individual reactor is lowered.

As a result of the use, according to the invention, of the honeycomb monolithic catalyst supports which, according to a particularly advantageous embodiment of the invention, are charged into a reactor with the catalytically effective activity increasing in the direction of flow, the reaction can be carried out with better control and the formation of hot spots can be largely suppressed.

The use of the monolithic catalysts according to the invention thus increases the selectivity of selective chlorination reactions and/or oxychlorination reactions and minimizes the rate of combustion, which ultimately leads to a higher yield of desired product. Surprisingly, the feared coke depositions also disappear.

Preferably, the catalyst supports to be used according to the invention are employed for catalyst for the production of chlorinated hydrocarbons by selective chlorination or oxychlorination of, for example, ethylene and/or ethane.

The illustrative examples which follow and the figures serve for further explanation of the invention.

EXAMPLE 1

Figure 1:
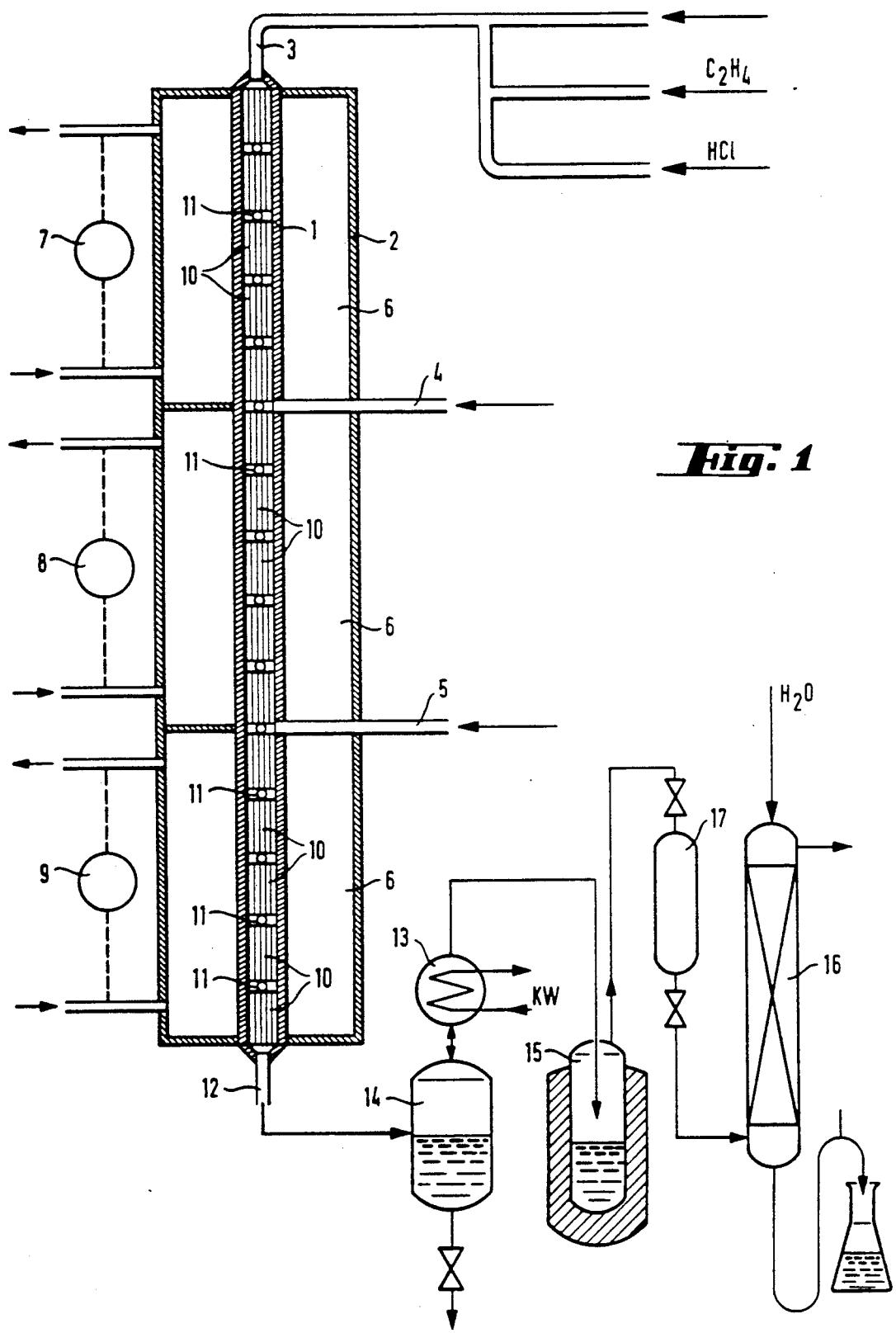
FIG. 1 is a diagrammatic longitudinal section through a reaction tube charged with the catalyst support according to the invention, and the experimental equipment used in the examples which follow.

The reactor according to FIG. 1 consists of an upright nickel tube 1 to 25 mm internal diameter and 2000 mm length, which is surrounded by a jacket 2 of steel. The reactor has three feed lines, the feed line 3 being located at the upper end and two further feed lines being arranged on the side after the first third (feed line 4) and second third (feed line 5) of the reaction tube. Thermostatically controlled heating oil is circulated in the hollow space 6 between then nickel tube 1 and the steel jacket 2 which is divided vertically into three segments (cooling zones). The temperatures in the heating/cooling circulations of each segment are separately controllable by the controller elements 7, 8 and 9. The temperature is maintained at 215° C. in the upper zone. The reaction tube 1 is charged with catalyst modules 10, 115 mm long in such a way that one glass sphere 11 of 3 mm diameter is located between the modules (except at the reactor inlet and outlet, where no glass spheres are required). The circular diameter of the catalyst modules was such that the modules can just be pushed into the reaction tube. The support modules have a central 5 mm hole; into which a thermowell provided with a thermocouple is introduced for recording the temperature profile. The ceramic modules had 200 channels per cross-section and the outer geometrical surface of the ceramic modules was covered by an eight-fold coating with a 200 μm layer of γ-$Al_2O_3$ and impregnated with $CuCl_2$ and KCl in accordance with the following loading pattern from the top downwards):

3 modules with 6% of $CuCl_2$ and 3% of KCl (35 cm height)
2 modules with 19% of $CuCl_2$ and 1.8% of KCl (23 cm height)
3 modules with 10% of $CuCl_2$ and 3% of KCl (35 cm height)
2 modules with 19% of $CuCl_2$ and 1.8% of KCl (23 cm height)
5 modules with 19% of $CuCl_2$ and 1.8% of KCl (58 cm height)

The percentage of salt is % by weight.

The individual gas streams are fed in via calibrated rotameters. (100) One Hundred liters (S.T.P.)/hour of hydrogen chloride and 58 liters(S.T.P.)/hour of ethylene are first mixed and then charged together with 57 liters(S.T.P.)/hour of air via line 3 to the upper part of the reactor. A further 57 liters(S.T.P.)/hour of air and 30 liters(S.T.P.)/hour of air, respectively, are fed via lines 4 and 5. The product mixture leaving the reactor via line 12 is cooled with water in the high-efficiency cooler 13, partial condensation taking place. The liquid phase is separated off in the separator 14. The gas stream is cooled to −25° C. in the cold trap 15 and washed free of HCl in the water scrubber 16. The condensates from the separator 14 and the cold trap 15 are collected and analyzed by gas chromatography, after the aqueous phase has been separated off. Using the gas-sampling vessel 17, the exit gas from the cold trap 15 is tested for CO and $CO_2$ by gas chromatography. The HCl conversion is calculated from the HCl content in the aqueous outflow from the water scrubber 16.

COMPARISON EXAMPLE 1:

The procedure followed is analogous to that in Example 1, but with the exception that, in place of the modules according to the invention, a conventional supported catalyst of spherical shape (diameter 4 to 5 mm; according to DE-A 2,630,938) with γ-$Al_2O_3$ as the support material is used. The particular Cu/K ratio corresponded to the following loading pattern (from the top downwards)

35 cm of γ-$Al_2O_3$ spheres with 6% of $CuCl_2$ and 3% of KCl

Figure 2:
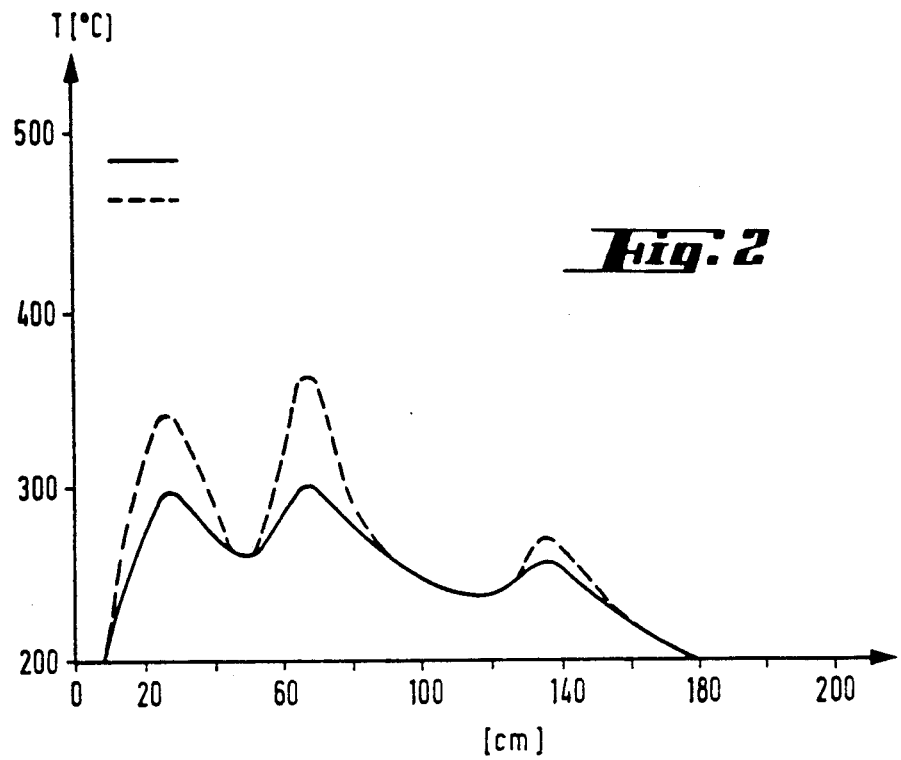
FIG. 2 is a plot of the temperature profile of the reaction zone in the process of Example 1 and comparison Example 1.
Figure 3:
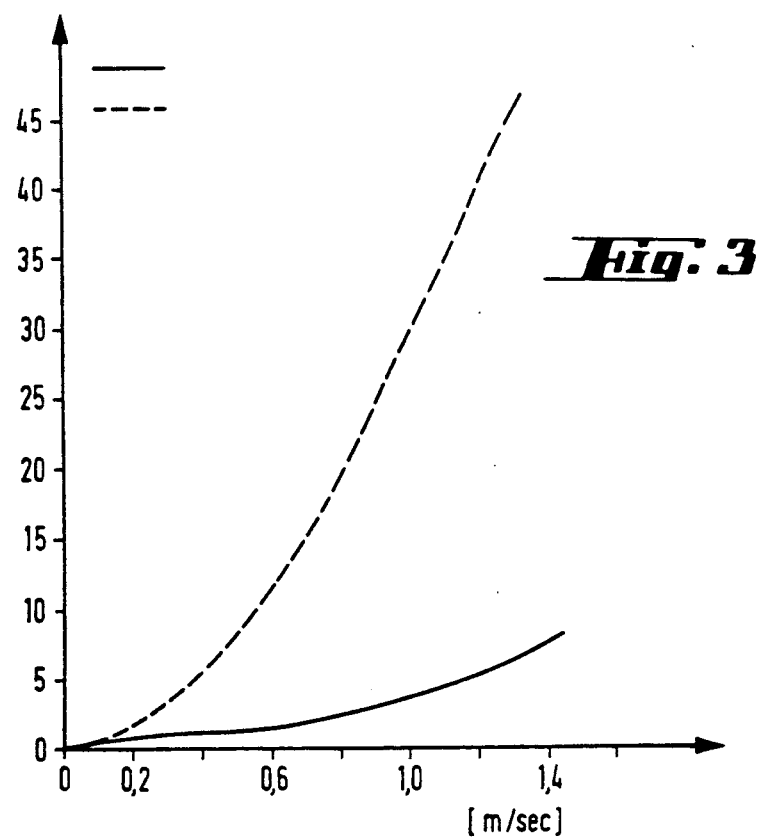
FIG. 3 is a plot of the pressure drop across the reactor as a function of gas velocity for the monolithic catalyst of Example 1 and the catalyst of comparison Example 1.

-continued 23 cm of γ-$Al_2O_3$ spheres with 19% of $CuCl_2$ and 1.8% of KCl
35 cm of γ-$Al_2O_3$ spheres with 10% of $CuCl_2$ and 3% of KCl
23 cm of γ-$Al_2O_3$ spheres with 19% of $CuCl_2$ and 1.8% of KCl
58 cm of γ-$Al_2O_3$ spheres with 19% of $CuCl_2$ and 1.8% of KCl In FIG. 2 and FIG. 3, the temperature profiles and pressure drops of the process according to Example 1 and Comparison Example 1, respectively, are shown.

It is clear that the use of the catalyst supports according to the invention as compared with a conventional form of support leads to considerably improved heat dissipation in the oxychlorination zone (FIG. 2) and the pressure drops in the reactor are lowered drastically (FIG. 3).

In Table 1, the analytical results with respect to conversion rate, selectivity and combustion rate in Example 1 and Comparison Example 1 are shown.

The comparison in Table 1 shows the great technical advance which is achieved when the catalyst modules provided according to the invention are employed for the reaction. The lower combustion rate, expressed as the CO content and $CO_2$ content in the exit gas, and the higher selectivity at the same HCl conversion, expressed as the 1,2-dichloroethane content in the organic condensate, show the superiority of the catalyst modules to be used according to the invention as compared with the conventional supported catalysts of spherical shape, hitherto used for this reaction.

TABLE 1

|  | Example 1 | Comparison Example 1 |
|---|---|---|
| Organic condensate | 149.1 cm$^3$/h | 148.6 cm$^3$/h |
| Aqueous condensate | 36.8 cm$^3$/h | 36.7 cm$^3$/h |
| Vent gas flow | 145.9 l(S.T.P.)/h | 145.8 l(S.T.P.)/h |
| HCl conversion | 85.2% | 85.1% |
| Exit gas analysis |  |  |
| $CO_2$ | 0.78% by volume | 1.45% by volume |
| CO | 0.93% by volume | 1.74% by volume |
| Analysis of the organic condensate |  |  |
| ethyl chloride | 0.095% by weight | 0.105% by weight |
| trans-1,2-dichloro-ethylene | 0.033% by weight | 0.051% by weight |
| 1,1-dichloroethane | 0.019% by weight | 0.018% by weight |
| carbon tetra-chloride | 0.285% by weight | 0.337% by weight |
| cis-1,2-dichloro-ethylene | 0.095% by weight | 0.149% by weight |
| chloroform | 0.060% by weight | 0.245% by weight |
| 1,2-dichloroethane | 97.43% by weight | 95.66% by weight |
| chloral | 0.187% by weight | 0.218% by weight |
| 1,1,2-trichloro-ethane | 1.70% by weight | 3.09% by weight |

What we claim is:

1. In a process for the production of chlorination hydrocarbons by a chlorination or an oxychlorination reaction, wherein a gaseous hydrocarbon to be chlorinated and a gaseous chlorinating agent or a gaseous oxychlorinating agent are contacted at an elevated temperature with a catalyst in a catalytic reaction zone, the improvement which comprises conducting said process in the presence of a monolithic, honeycomb catalyst support with a longitudinal axis and having a length of up to 20 cm, and a diameter of from 20 to 50 mm, said catalyst support having from 10 to 100 channels per cm$^2$, and each channel having a diameter of from 0.1 to 5.0 mm and arranged parallel to the longitudinal axis and open at both ends of the support, the support having a chlorination or oxychlorination catalytic material coated on its surface.

2. A process of claim 1 wherein the monolithic catalyst support has a diameter to length ratio of from 1:5 to 1:10.

3. A process of claim 1 wherein the catalyst support coated with the catalytic material is arranged in a single series in a temperature controlled tubular reaction zone wherein the catalyst support substantially occupies the entire cross-section of the reaction zone.

4. A process of claim 2 wherein the catalyst support coated with the catalytic material is arranged in a single series in a temperature controlled tubular reaction zone wherein the catalyst support substantially occupies the entire cross-section of the reaction zone.

5. A process of claim 3 wherein spherical packing is interposed between at least some of the series arranged catalyst supports.

6. A process of claim 4 wherein spherical packing is interposed between at least some of the series arranged catalyst supports.

7. A process of claim 1 wherein the catalytic supports are arranged in the reaction zone so that the amount of catalytic material coated on the catalytic support increases in the direction of flow of the reactants.

8. A process of claim 2 wherein the catalytic supports are arranged in the reaction zone so that the amount of catalytic material coated on the catalytic support increases in the direction of flow of the reactants.

9. A process of claim 3 wherein the catalytic supports are arranged in the reaction zone so that the amount of catalytic material coated on the catalytic support increases in the direction of flow of the reactants.

10. A process of claim 4 wherein the catalytic supports are arranged in the reaction zone so that the amount of catalytic material coated on the catalytic support increases in the direction of flow of the reactants.

11. The process of claim 1 wherein the gaseous hydrocarbon is ethylene.

12. The process of claim 1 wherein the gaseous hydrocarbon is ethane.

* * * * *